United States Patent
Kadono et al.

(12)

(10) Patent No.: US 6,267,993 B1
(45) Date of Patent: *Jul. 31, 2001

(54) PLANT-DERIVED POWDER AND AN EXTRACT OF THE SAME

(76) Inventors: Toshiko Kadono, 5-19, Ichinoe 7-chome, Edogawa-ku Tokyo 132; Yoshihiro Sekino, 8-9, Daigiri 2-chome, Fujisawa-shi, Kanagawa 251; Zenichi Ogita, 25, Akaecho 7-chome, Toyama-shi, Toyama 930, all of (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/951,471

(22) Filed: Oct. 16, 1997

Related U.S. Application Data

(62) Continuation of application No. 08/892,239, filed on Jul. 14, 1997, now abandoned, which is a continuation of application No. 08/525,524, filed as application No. PCT/JP95/00059 on Jan. 20, 1995, now abandoned.

(30) Foreign Application Priority Data

Jan. 20, 1994 (JP) .................................................. 6-21895

(51) Int. Cl.$^7$ .................................................. A61K 35/78
(52) U.S. Cl. ........................... 424/769; 424/774; 424/778
(58) Field of Search ............................... 424/195.1, 769, 424/774, 778

(56) References Cited

U.S. PATENT DOCUMENTS

| | | | | |
|---|---|---|---|---|
| 4,285,930 | * | 8/1981 | Likhite .................................... | 424/92 |
| 4,986,985 | | 1/1991 | Grossman et al .................. | 424/195.1 |
| 5,389,370 | | 2/1995 | O'Reilly et al. ................... | 424/195.1 |
| 5,411,733 | * | 5/1995 | Hozumi et al. .................... | 424/195.1 |

FOREIGN PATENT DOCUMENTS

| | | |
|---|---|---|
| 62-142181 | * 6/1987 | (JP) . |
| 2-172922 | 7/1990 | (JP) . |
| 3-72490 | 3/1991 | (JP) . |
| 4-36244 | 2/1992 | (JP) . |
| 1187825 | 5/1983 | (SU) . |
| 91/6311 | 6/1991 | (WO) . |

OTHER PUBLICATIONS

Zhen Minshi: "An Experimental Study of Antiviral Action of 472 Herbs on Herpes Simplex Virus", Journal of Traditional Chinese Medicine, vol. 8, No. 3, Sep. 1988, pp. 203–206.
Mitsuya et al., Nature, 325:773–778, 1987.*
Kakiuchi et al., J. Natural Products, 48:614–621, Derwent Abstract, 1985.*
Courthout et al., Dissertation Abstracts International, 53(3B):1313, 1991.*
Barre–Sinoussi et al., Science, 220:868–871, 1983.*
Gallo et al., Science, 224:500–503, 1984.*
Baltimore, D., Nature, 226:1209–1211, 1970.*
Temin et al., Nature, 226:1211–1213, 1970.*
Meek et al., Nature, 343:90–92, 1990.*
E. Eich, ACS Symposium Series, American Chemical Society, 691:83–96, 1998.*
S.J. Martin, The Biochemistry of Viruses, Cambridge University Press, Chapter 7, pp. 130–138, 1978.*
Domingo et al., Genetic Engineering, Principles and Methods, vol. 14, ed. J.K. Setlow, Plenum Press, NY, pp. 13–31, 1992.*
Pauwels et al., J. Recept. Signal Transduction Res., 15:606–616, 1995.*
Evans, in Trease and Evans' Pharmacognosy, 13th Ed., Bailliere Tindall, London, England, pp. 79–92, 1989.*
Remington's Pharmaceutical Sciences, Mack Publishing Company, Easton, PA, pp. 1256–1267, 1980.*

* cited by examiner

*Primary Examiner*—Christopher R. Tate
*Assistant Examiner*—Janet M. Kerr
(74) *Attorney, Agent, or Firm*—McDermott, Will & Emery

(57) ABSTRACT

A medicinal plant-derived antiviral powder is provided as obtained by collecting a medicinal plant having an antiviral action, immediately quickly heating the plant to de-activate enzymatic activity, subjecting to low temperature drying, and milling after the quick heating or low temperature. The powder may be extracted with hot water or a lower alcohol to obtain antiviral extract. These powder and extract may be utilized as preparations, particularly, a powder, comprising an effective amount thereof The powder and extract obtained by treating, as a medicinal plant, young leaves of *Rhus verniciflua* and a flower portion of *Ulmus davidiana var.japonica* are useful.

12 Claims, No Drawings

PLANT-DERIVED POWDER AND AN EXTRACT OF THE SAME

This application is a continuation of application Ser. No. 08/892,239, filed Jul. 14, 1997, now abandoned, which is a continuation of Ser. No. 08/525,524 filed Sep. 19, 1995, now abandoned, which is a 371 application of PCT/JP95/00059, filed Jan. 20, 1995.

FIELD OF THE INVENTION

This invention relates to an antiviral powder obtained from a medicinal plant having an antiviral action, an antiviral extract obtained from the powder, and a preparation comprising the powder and/or extract.

BACKGROUND OF THE INVENTION

In the history of human beings who have suffered with various bacterial and viral infections from old, the discovery of antibiotics and the development of vaccines against viruses have brought about a great development in the medical care of this century. However, many chronic and infectious diseases have still presented a serious social problem.

More particularly, the greatest problem which confronts us today includes prophylaxis of infection with viruses such as human immunodeficiency virus (abbreviated as HIV; Barre-Sinoussi et al., 1983; Gallo et.al., 1984) which causes human adult T-cell leukemia (abbreviated as HALT) and human T-cell lymphotropic virus (abbreviated as HTLV; Yoshida et al., 1984) which causes acquired immunological deficiency syndrome (abbreviated as AIDS) and the treatments of theses diseases.

Some of herb medicines and crude drugs constituting the herb medicines have been hitherto believed as having the antiviral action. In recent years, a number of studies and reports have been made on crude drugs having the antiviral action. The antiviral activity itself has been elucidated on about half of the crude drugs, thus leaving many crude drugs to be unclear with respect to the activity. The mechanism of the antiviral action has now been under detailed study. Some reports have been already made on the antiviral action through an immunological regulation activity system.

On the other hand, there is the possibility of developing antiviral agents along the line of the central dogma of the molecular biology, i.e. the flow of deoxyribose nuleic acid (abbreviated as DNA)→messenger ribonucleic acid (abbreviated as mRNA)→protein.

Additionally, transcription that takes place in the direction opposite the central dogma, i.e. from RNA to DNA (in contrast to the central dogma's flow of DNA to mRNA) also occurs in nature. This has been backed up with the discovery of a reverse transcriptase (abbreviated as RT) made by Temin and Baltimore in 1970 (Baltimore, 1970; Temin and Mizutani, 1970).

Retroiviruses (reverse transcriptase contains oncovirus) are those having reverse transcriptases as is suggested by the name. Specific attention has been paid to the virus since the retroviruses were recognized in 1980's as causing human adult T-cell leukemia and AIDS, whose spread has been viewed with anxiety.

Since then, extensive studies have been made on retroviruses. At present, detailed information has been reported at a gene level and the life cycles of the viruses are now being made clear (Meek et al., 1990a).

The target in the development of antiviral agents is considered to reside in a method of suppressing the attachment of viruses to cells and suppressing the reverse transcription of viral ribonucleic acid toward deoxyribonucleic acid. Typical compounds reported as having the activity of inhibiting reverse transcription include nucleotides, antibiotics, natural products and the like.

Of these, nucleotide derivatives are greatest in number and have been synthesized for the purpose of the competitive inhibiting action of the reverse transcriptase substrate (Nhtsuya and Broder, 1987)

Azidothymidine, 2',3'-dideoxycytidine and 2',3'-dideoxyinosin are typical of these reverse transcriptase inhibitors and are a few medicines authorized as agents for treating for AIDS.

SUMMARY OF THE INVENTION

An object of the invention is to provide an antiviral powder capable of inhibiting the enzymatic activity of reverse transcriptases and derived from medicinal plants, and an antiviral extract extracting an inhibiting component from the powder.

Another object of the invention is to provide an antiviral powder which has an inhibiting action on HIV-I reverse transcriptase, which is a pathogen of AIDS, and also on a reverse transcriptase derived from mouse leukemia virus.

A further object of the invention is to provide an antiviral preparation which comprises the powder and/or extract set out above.

DETAILED DESCRIPTION OF THE INVENTION

The antiviral powder of the invention derived from a medicinal plant is one obtained according to the following procedure. Immediately after collection of a medicinal plant starting material having the antiviral action, the starting material is quickly heated under conditions sufficient to de-activate the enzymatic activity of the starting material, followed by drying the quickly heated plant at a low temperature of from −5° C. to +10° C. to an extent that a moisture content is not higher than 10% to obtain a powder of the medicinal plant. For obtaining a powder, the medicinal plant is milled or powdered at a stage after the quick heating or after the low temperature drying.

In order to obtain an antiviral extract, the powder of the medicinal plant is subjected to extraction with hot water or a lower alcohol. If necessary, the extract may be appropriately concentrated.

In the practice of the invention, a preparation comprising the powder and/or extract as an effective component is also provided. The preparation may be formulated as an emulsion, oil, wettable powder, powder or the like. Preferably, a powder is used.

The present invention is described in detail.

The starting medicinal plants used to obtain the antiviral powder or extract of the invention and having the antiviral action may be any medicinal plants provided that they have the antiviral activity. All sites or portions of the medicinal plant containing an antiviral component may be usable including leaf, stem, root, flower and the like. Especially, the leaves and, preferably, young leaves of Japanese lacquer (*Rhus verniciflua*) and the flower portion of *Ulmus davidiana var.japonica* are preferably used as having a remarkable reverse transcriptase inhibiting action. It will be noted that the term "young leaves" used herein means ones which are in a soft condition and which generally are not older than 8 weeks in age, preferably not older than 4 weeks. The above definition concerning the young leaves should not be construed as limitative because the Japanese lacquer greatly differs in the rate of growth depending on the growing district.

In order to obtain the antiviral powder, the certain portions of the medicinal plant are collected. Immediately after the collection, the portions are subjected to quick heating. The term "immediately after collection" is intended to mean that the portions collected are subjected to quick heating within 3 minutes to about 30 minutes after the collection. The immediate quick heating can, to an extent, prevent an effective component form being decomposed by enzymes. The terms "quick heating under conditions sufficient to de-activate enzymatic activity" means that when using, for example, a pressure drum heater, the starting material is thermally treated at a temperature ranging from 80 to 140° C. within 2 minutes, preferably for approximately one minute, and more preferably for 40~50 seconds. Alternatively, a heater such as a microwave oven may also be used. In the case, with an output power of 600 W, the active enzymes can be de-activated by heating for 20 to 50 seconds although depending on the amount of starting material. The quick heating should be carried out under conditions of de-activating a lytic enzyme or enzymes in the starting material but not decomposing other components of the medicinal plant. Since the lytic enzyme is de-activated or broken down, the decomposition of the other components with the lytic enzyme can be prevented, thereby preventing a lowering in amount of effective components.

The thus quickly heated starting material is subsequently subjected to low temperature drying. The low temperature drying is performed within a range of −5 to 10° C. The drying at low temperatures can prevent decomposition in the drying step of the medicinal plant components including an effective component or components. The low temperature drying is continued until the content of moisture in the starting material is not higher than 10 wt %, preferably from 2 to 5 wt %.

For the low temperature drying, one or both of a hot air or air dryer and an ice temperature dryer is used to dry the material within the above-defined temperature range.

The ice temperature dryer is commercially available, for example, from Nippon Light Metal Co., Ltd., as having the following specification.

Temperature range: −50° C.~+10° C.
Humidity range: 50~80% (temperature of 0° C.~−5° C.)
Air velocity: 1~8 m/second The dimension of the ice temperature drying chamber of the dryer is 96 cm×53 cm×59 cm and the capacity of a refrigerator is 2.2 kW with a cooling medium being, for example, Flon Q22.

The hot air dryer includes, for example, a far infrared ray dryer. If this far infrared ray dryer is used, the s material is subjected to ice temperature drying after completion of the far infrared ray treatment.

The thus dried material is milled by a usual milling device, such as, for example, a colloid mill, to a size of 50 to 100 mesh μm. Alternatively, the materials may be finely cut into powder.

The milling or cutting may not be necessarily performed after completion of the low temperature drying but may be effected after completion of the quick heating. The milling step may be appropriately changed as desired.

The thus obtained antiviral powder may be used as it is or an effective component may be extracted with hot water or a lower alcohol. In the latter case, the low temperature drying is not necessarily required, i.e. the extraction may be effected after the quick heating. For the extraction, an ordinarily employed extractor such as the Soxhlet extractor is used wherein hot water or a lower alcohol is refluxed. Examples of the lower alcohol include aqueous solutions of 30 to 50% of methyl alcohol or ethyl alcohol. The extraction is generally continued for 30 to 60 minutes under reflux. The resultant extract may be concentrated to a level of about 0.1 wt %.

The concentrated extract is a kind of soft extract, is unlikely to handle as it is and should preferably used in the form of a diluted preparation.

More particularly, the powder or extract of the invention may be used in the form of various preparations as having set out hereinbefore and should preferably be use as a powder or wettable powder. Where the antiviral powder or extract is employed in the form of a powder or wettable powder, starch, lactose, dextrin and the like are used as an adjuvant. In this case, the antiviral powder and/or extract is contained in an effective amount. Preferably, the content is not less than 1 wt %, more preferably not less than 10 wt %, of a preparation composition. This content is applicable to other types of preparations.

The Inhibiting action of the antiviral powder and/or extract of the invention has been investigated as set out in examples appearing hereinafter. Different types of medicinal plants have been treated according to the procedure set out hereinbefore and subjected to screening by use of a reverse transcriptase derived from an avian myeloblastosis virus (usually abbreviated as AMV), followed by testing components found to inhibit AMV RT against a reverse transcriptase of HIV-1 (the putative pathogenic agent in AIDS.) Moreover, the comparison with the inhibiting action on the reverse transcriptase derived from murine leukemia virus (abbreviated as MULV). As a result, it has been found that the young leaf portions of the Japanese lacquer which are not older than 8 weeks in age, more preferably 4~ 5 weeks, and the flower portion of *Ulmus davidiana var.japonica* exhibit a good inhibiting effect.

The invention is more particular described by way of examples and preparation examples.

EXAMPLE 1

The effect of plants belonging to the Rhus of Anacardiaceae on inhibition of the reverse transcriptases was checked. Young leaves of *Rhus verniciflua, Rhus trichocarpa, Rhus ambigna, Rhus javanica,* and *Rhus sylverstris* were, respectively, collected. Immediately, these leaves were subjected to quick heating for 50 seconds in a microwave oven of 600 W. Thereafter, the leaves were dried at a temperature of 10° C. and milled to obtain powders of the powders obtained in respective starting materials. 10 mg of the respective powders obtained in this manner manner was extracted with 10 ml of hot water for 1 hour. Each hot water extract was checked with respect to the reverse transcriptase inhibiting action according to the following procedure. More particularly, each extract was centrifugally separated to obtain a supernatant liquid, the supernatant was adjusted in such a way that a final concentration of plant-derived solute in a reaction system was at 50.5 μg/ml, and then the supernatant was subjected to an RT (reverse transcriptase) inhibition assay. The results are shown in Table 1. This table shows the results of the RT inhibition action of the leaf portions of the respective samples wherein a smaller value exhibits a better inhibiting action.

TABLE 1

Effect of Plants Belonging to Rhus of Anacardiaceae on Inhibition of Reverse Transcriptase (IC 50/µg/ml)

| | |
|---|---|
| Rhus verniciflua | 4 ~ 5 |
| Rhus trichocarpa | 50 |
| Rhus ambigna | 40 |
| Rhus javanica | 20 ~ 40 |
| Rhus sylvestris | 20 ~ 40 |

The above results reveal that the hot water extract of the leaves of the *Rhus verniciflua* exbibit a good reverse transcriptase inhibiting effect. However, the hot water extracts of the other plants belonging to the Rhus of Anacardiaceae have no significant reverse transcriptase effect.

EXAMPLE 2

Young and old leaves of the *Rhus verniciflua* and young and old leaves and a flower portion of *Ulmus davidiana var.japonica* were, respectively, used and treated in the same manner as in Example 1 provided that the extraction was effected using both hot water and an aqueous solution of 30% ethyl alcohol. The results are shown in Table 2.

TABLE 2

Effect of *Rhus verniciflua* and *Ulmus davidiana var. japonica* on Inhibition of Reverse Transcriptase (IC 50/µg/ml)

| | hot water extract | extract with ethyl alcohol |
|---|---|---|
| young leaves of *Rhus verniciflua* (note 1) | ≦4 ~ 5 | ≦4 ~ 5 |
| old leaves of *Rhus verniciflua* | 100 | 100 |
| young leaves of *Ulmus davidiana var. japonica* | 50 | 50 |
| old leaves of *Ulmus davidiana var. japonica* | 100 | 100 |
| flower of *Ulmus davidiana var. japonica* | 20 | 20 |

(Note 1)
The young leaves of *Rhus verniciflua* were collected at about the middle of March at Wajima city of Ishikawa Prefecture with their length being 5 ~ 6 cm.

The above results reveal that the reverse transcriptase inhibiting effect is recognized in the hot water extract and the lower alcohol extract (30% ethyl alcohol) of the powders obtained after the quick heating of the young leaves of *Rhus verniciflua*, but is not recognized for the respective extracts of the old leaves of *Rhus verniciflua*.

On the other hand, the flower portion of *Ulmus davidiana var.japonica* has a reverse transcriptase inhibiting effect although not so great.

EXAMPLE 3

In this example, a mixture of the young leaves of *Rhus verniciflua* and the flower portion of *Ulmus davidiana var.japonica* was checked with respect to the reverse transcriptase inhibiting effect.

More particularly, collected young leaves of *Rhus verniciflua* and flower portion of *Ulmus davidiana var.japonica* were immediately quickly heated in a microwave oven of 600 W. The young leaves and the flower portion were mixed at ratios of 1:1 (sample 1), 2:1 (sample 2) and 1:2 (sample 3). Each sample was dried at a low temperature in a drying device, followed by millng. The extracts of the samples with hot water and 30% ethyl alcohol were subjected to measurement of the reverse transcriptase inhibiting action. The results are shown in Table 3.

TABLE 3

Effect of Extracts of Mixtures of Young Leaves of *Rhus verniciflua* and Flower Portion of *Ulmus davidiana var. japonica* on Inhibition of Reverse Transcriptase (IC 50/µg/mg)

| | hot water extract | extract with ethyl alcohol |
|---|---|---|
| sample 1 | 5 | 5 |
| sample 2 | 2 ~ 3 | 2 ~ 3 |
| sample 3 | 3 ~ 4 | 3 ~ 4 |

From the above results, it will be seen that the extracts of the mixtures of the young leaves of *Rhus verniciflua* and the flower portion of *Ulmus davidiana var.japonica* improve the inhibition effect presumably by the synergistic effect of the mixture. Accordingly, the mixed extract is a preferred one of the invention.

<Preparation Example 1>
Dry powder of 10% young leaves of *Rhus verniciflua* (1:10 dilution)

| | |
|---|---|
| Dry powder of young leaves of *Rhus verniciflua* | 100 g |
| 0.1% Blue No. 1 aluminium lake lactose | 0.1 g |
| Lactose | balance |
| Total amount | 1000 g |

<Preparation Example 2>
Powder of 10% of a mixture of young leaves of *Rhus verniciflua* and flower portion of *Ulmus davidiana var. japonica* (1:10 dilution)

| | |
|---|---|
| Extract of young leaves of *Rhus verniciflua* | 100 g |
| Extract of flower portion of *Ulmus davidiana var. japonica* | 50 g |
| Starch | balance |
| Total amount | 1000 g |

The 1:10 dilution of the antiviral powder of the invention or a 1:100 dilution of an antiviral extract obtained from a viscous extract prepared by thermally extracting the antiviral powder with 30% ethyl alcohol and concentrating the extract did not lower in the reverse transcriptase inhibiting action, thus the effect thereof being recognized.

What is claimed is:

1. A plant-derived powder having in vitro reverse transcriptase inhibiting activity, obtained by a process comprising:

collecting a plant stalling material, which starting material is selected from the group consisting of leaf portions of verniciflua not older than eight weeks in age, flower portions of *Ulmus davidiana var.japonica*, and mixtures thereof;

immediately subjecting the plant starting material to quick heating under conditions sufficient to de-activate enzymatic activity in the portions to produce a quickly heated material;

drying the quickly heated material at −5° C. to +10° C. until the quickly heated material has a moisture content of not higher than 10% by weight; and milling the quickly heated material either after the quick heating step or after the drying at a low temperature;

to produce the plant-derived powder.

2. A plant-derived powder as defined in claim 1, wherein said starting material consists of a flower portion of *Rhus verniciflua*.

3. A plant-derived powder as defined in claim 1, wherein said starting material consists of a flower portion of *Ulmus davidiana var.japonica*.

4. A plant-derived powder as defined in claim 1, wherein said starting material is subject to quick heating within 30 minutes after the collection of said starting material.

5. A plant-derived powder as defined in claim 1, wherein said starting material is quickly heated within two minutes after collection of said starting material.

6. A composition comprising an amount of the powder defined in claim 1 effective to inhibit reverse transcriptase.

7. The composition as defined in claim 6, having a composition weight, wherein the amount of the powder is not less than 1 wt % of the composition weight.

8. A plant-derived extract, obtained by a process, comprising:

collecting a plant starting material, which starting material is selected from the group consisting of leaf portions of *Rhus verniciflua* not older than eight weeks in age, flower portions of *Ulmus davidiana var.japonica*, and mixtures thereof;

immediately subjecting the plant starting material to quick heating under conditions sufficient to deactivate enzymatic activity in the portions to produce a quickly heated material;

drying the quickly heated material at −5° C. to +10° C. until the quickly heated material has a moisture content of not higher than 10% by weight;

milling the quickly heated material either after the quick heating step or after the drying at low temperature to produce a plant-derived powder; and extracting the plant-derived powder with hot water or a lower alcohol to produce the extract.

9. The extract as defined in claim 8, wherein said starting material consists of leaves not older than eight weeks in age of *Rhus verniciflua*, a flower portion portion of *Ulmus davidiana var.japonica,* or mixtures thereof.

10. A composition comprising an amount of the extract defined in claim 8 effective to inhibit reverse transcriptase.

11. The composition as defined in claim 10 having a composition weight, wherein the amount of extract is not less than 1 wt % of the composition weight.

12. A concentrated extract obtained by a process comprising:

collecting a plant starting material, which starting material is selected from the group consisting of leaf portions of *Rhus verniciflua* not older than eight weeks in age, flower portions of *Ulmus davidiana var.japonica*, and mixtures thereof;

immediately subjecting the plant starting material to quick heating under conditions sufficient to deactivate enzymatic activity in the portions to produce a quickly heated material;

drying the quickly heated material at −5° C. to +10° C. until the quickly heated material has a moisture content of not higher than 10% by weight;

milling the quickly heated material either after the quick heating step or after the drying at low temperature to produce a plant-derived powder;

extracting the plant-derived powder with hot water or a lower alcohol to produce an extract; and concentrating the extract to form the concentrated extract.

* * * * *

UNITED STATES PATENT AND TRADEMARK OFFICE
CERTIFICATE OF CORRECTION

PATENT NO. : 6,267,993 B1
DATED : July 31, 2001
INVENTOR(S) : Kadono Toshiko et al.

It is certified that error appears in the above-identified patent and that said Letters Patent is hereby corrected as shown below:

Title page,
After the data in the inventor section "[76]", insert
-- [73] Assignee: Masahito Hoashi,
　　　　　　　　52-15-723, Nakano 5-Chome, Nakano-Ku,
　　　　　　　　Tokyo (JP) --;

Under Item "[62] Related U.S. Application Data", after "08/525,524",
Replace "filed as application No." with -- filed Sep. 19, 1995, which is a 371 Application of --.

Signed and Sealed this

Twentieth Day of November, 2001

Attest:

*Nicholas P. Godici*

NICHOLAS P. GODICI
*Acting Director of the United States Patent and Trademark Office*

*Attesting Officer*